United States Patent [19]

Wachter et al.

[11] Patent Number: 5,445,008
[45] Date of Patent: Aug. 29, 1995

[54] MICROBAR SENSOR

[75] Inventors: Eric A. Wachter, Oak Ridge; Thomas G. Thundat, Knoxville, both of Tenn.

[73] Assignee: Martin Marietta Energy Systems, Inc., Oak Ridge, Tenn.

[21] Appl. No.: 217,411

[22] Filed: Mar. 24, 1994

[51] Int. Cl.⁶ ............................................. G01N 27/00
[52] U.S. Cl. .................................. 73/24.06; 73/24.01; 422/88
[58] Field of Search .................... 422/83, 88; 310/312, 310/321, 330, 331; 73/24.01, 24.06, 31.05, 31.01, 31.03

[56] References Cited

U.S. PATENT DOCUMENTS

| | | | |
|---|---|---|---|
| 3,766,616 | 10/1973 | Staudte | 310/312 |
| 4,549,427 | 10/1985 | Kolesar, Jr. | 422/88 |
| 4,637,987 | 1/1987 | Minten et al. | 422/88 |
| 4,686,847 | 8/1987 | Besocke | 73/24.01 |
| 5,179,028 | 1/1993 | Vali et al. | 310/312 |
| 5,339,675 | 8/1994 | DiLeo et al. | 73/24.06 |

OTHER PUBLICATIONS

"Overview Of Chemical Microsensor Technology", Feb., 1988 Catalong, Microsensor Systems, Inc., P.O. Box 90, Fairfac, Va. 22030.
"Atomic Force Microscopy", D. Rujgar and P. Nansma, Physics Today, Oct., 1990, p. 23.
"Frequency Modulation Detection using High-Q Cantilevers For Enhanced Force Microscope Sensitivity", TR. Albrecht et al, J. Appl. Physics, vol. 69, Jan. 15, 1991, p. 668.
"Analysis and Improvement of the Kelvin Method For Measuring Differences In Work Function", J. S. W. de Boer et al, Rev. Sci. Instrum., vol. 44, No. 8, Aug., 1973, p. 1003.

Primary Examiner—Hezron E. Williams
Assistant Examiner—Michael J. Brock
Attorney, Agent, or Firm—W. Allen Marcontell; James M. Spicer; Harold W. Adams

[57] ABSTRACT

A mass microsensor is fabricated with a microcantilever oscillated by a piezoelectric transducer. A chemical coating having absorptive or adsorptive affinity for a specifically targeted chemical or compound is applied to the microcantilever for oscillation in the monitored atmosphere. Molecules of the targeted chemical attach to the microcantilever coating resulting in an oscillating mass increase which influences the resonant frequency of the microcantilever oscillation. The rate at which the coated microcantilever accumulates the target chemical is functional of the target chemical concentration. Consequently, the extent of microcantilever oscillation frequency change is related to the concentration of the target chemical within the monitored atmosphere. Such oscillation frequency changes are detected by a center-crossing photodiode which responds to a laser diode beam reflected from the microcantilever surface resulting in an output frequency from the photodiode that is synchronous with the microcantilever frequency.

20 Claims, 2 Drawing Sheets

MICROBAR SENSOR

BACKGROUND OF THE INVENTION

The U.S. Government has a paid-up license in this invention and the right in limited circumstances to require the patent owner to license others on reasonable terms as provided for by the terms of contract No. DE-AC05-84OR21400.

FIELD OF THE INVENTION

The present invention relates to instruments for measuring the vapor concentration of a predetermined chemical or compound dispersed within a monitored atmosphere.

DESCRIPTION OF THE PRIOR ART

A pressing need exists in many industries, disciplines and governmental interests for a highly sensitive and selective chemical vapor detector, particularly for organic vapors. To qualify, such a detector must have such diverse characteristics as being small, rugged, inexpensive, selective, reversible and extremely sensitive.

The prior art is substantially represented by only two sensor principles. One is the Surface Acoustic Wave (SAW) device and the other is the chemically sensitive Field Effect Transistor (Chem FET). Although these devices are reasonably inexpensive to produce, respective sensitivity in the nanogram per $mm^2$ range is less than desired.

Spectroscopic approaches to this technical objective such as surface-enhanced Raman scattering (SERS) devices offer nanogram to picogram sensitivity but inherently require complex optical support equipment and all the consequential expense.

Chromatographic methods of vapor concentration measurement also require bulky, expensive, fragile hardware and specialized consumables.

It is an object of the present invention, therefore, to teach the construction of a small, selective, inexpensive and highly sensitive vapor concentration detector.

Another object of the invention is to provide a vapor detection sensor that is sensitive in the sub-picogram range.

SUMMARY

These and other objects of the invention to be described or made apparent hereafter, are accomplished by the exploitation of two disparate physical principles comprising (a.) the resonant frequency sensitivity of an oscillating spring to the mass magnitude intimately coupled to the spring; and (b.) like chemicals dissolve or adsorb like chemicals. A piezoelectric vibrated cantilever bar, which is the "spring" in this system, is surface coated with a compound selective substance having substantially exclusive affinity for the targeted compound. As the coated cantilever element is vibrated in the monitored atmosphere, vapor phase molecules of the target compound attach to the cantilever coat to increase the oscillatory mass of the structure. Such mass increase results in a related resonance frequency change which is independently measured by the reflected beam from a laser diode received by a photodiode center-crossing detector signal source for a frequency counting circuit. The magnitude of the microcantilever frequency change is therefore proportional to the concentration of the targeted chemical or compound in the monitored atmosphere.

DESCRIPTION OF THE DRAWINGS

Relative to the drawings wherein like reference characters designate like or similar elements throughout the several figures of the drawings.

DESCRIPTION OF THE PREFERRED EMBODIMENT

Figure 1:
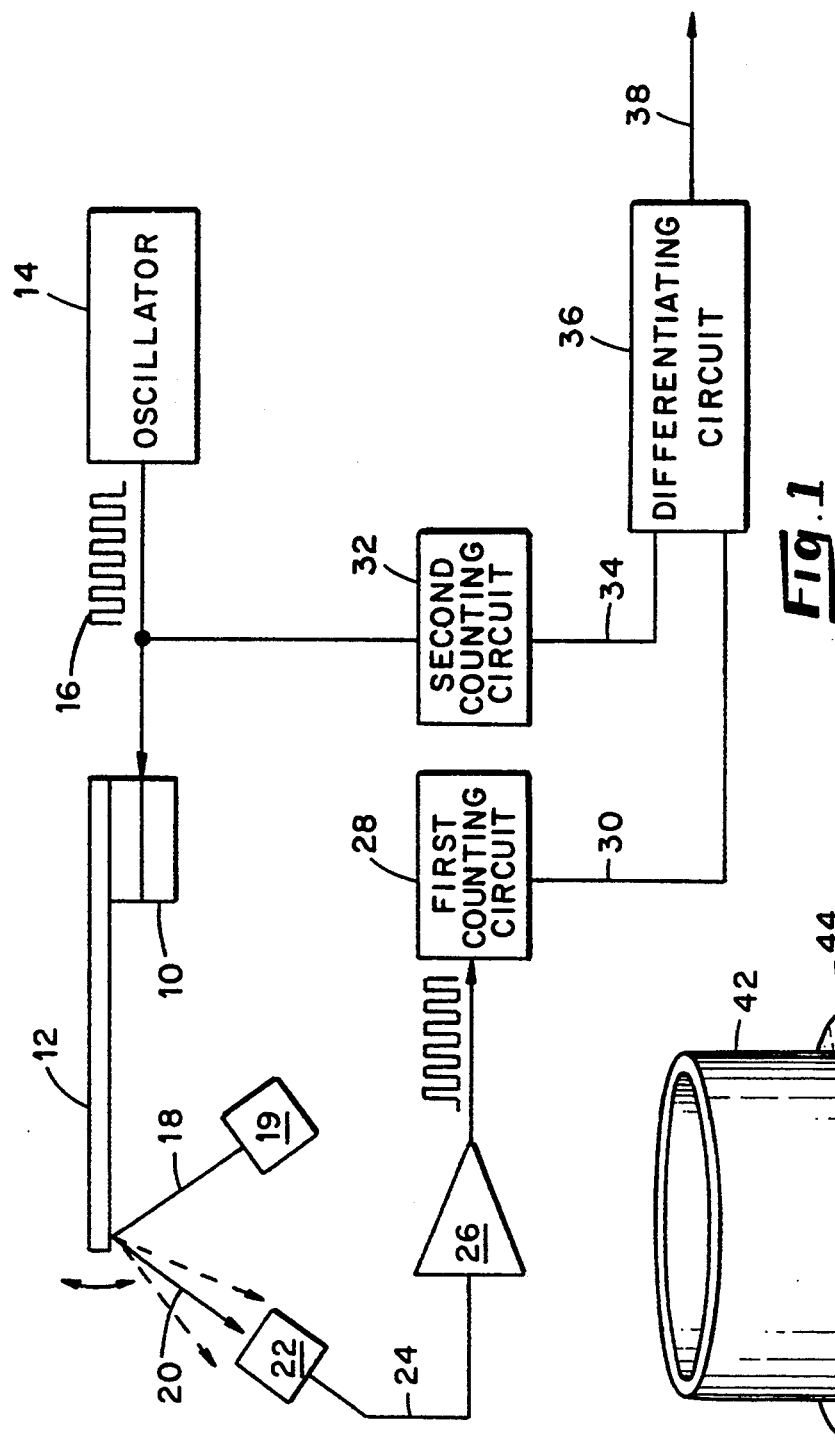
FIG. 1 is a pictorial schematic of the invention assembly and mechanical operation.

To illustrate the basic invention operating principles, reference is given to FIG. 1 wherein element 10 represents a piezoelectric transducer supporting the attached end of a microcantilever 12 fabricated of quartz or silicon, for example. Responsive to a master oscillator 14 drive signal 16, the microcantilever is driven by the piezoelectric transducer at a non-loaded resonance frequency. A laser beam 18 emitted by laser diode 19 is reflected from the clean underside of microcantilever 12. The sweep of such reflection 20 is detected by an optical detector 22 such as a photodiode. As the reflected beam 20 sweeps back and forth across the detector 22, it produces a repetitive signal 24 with a frequency proportional to the oscillation frequency 16 of the microcantilever. Photodiode signal 24 is amplified 26 and the sweep pulses counted over a predetermined time interval by a counting circuit 28. The interval count is the substance of signal 30 issued by counter 28.

Simultaneously, the drive signal 16 is monitored by a second counting circuit 32 to produce the drive frequency signal count 34. The values of signals 30 and 34 are compared by a differentiating circuit 36 to produce a resultant signal 38.

The small differences between signals 30 and 34 are proportionally related to changes in the oscillating mass of microcantilever 12 due to an accumulation of target chemicals or compounds on the microcantilever. Such accumulations are induced by chemically selective coatings applied to the surface of microcantilever 12. These chemically selective coatings provide sensitivity and selectivity. Selectivity will depend on how uniquely a specific vapor or class of vapors will interact with the coating.

Sensitivity will depend on the total increase in mass due to the absorbed vapor, and thus on the capacity of the coating for vapor as well as the coating thickness. The response time of the system will be dependent upon the coating thickness and the rate of gas diffusion into the coating.

Any number of methods may be used to apply these selective coatings to the surface of a microcantilever including deposition from solutions such as microsyringes, Q-tips, brushes, and application by spin casting, dipping air-brush spraying, Langmuir-Blodgett (L-B) film transfer, plasma deposition, sputtering, evaporation, sublimation and self-assembled monlayers (SAMs).

To the latter, SAMs are very inexpensive to produce but require covalent or very strong non-covalent bonding between the coating internal terminus and the microcantilever surface. This is most easily effected through the use of a metal-thiol linkage, wherein a derivatized thiol reacts with a metal film such as silver or gold deposited in a thin layer on the microcantilever surface to form a highly resilient chemical coating. Derivatization of the opposite terminus of the molecules is used to afford specificity for the target chemical or compound (analyte) by providing a surface that has chemical affinity for the target. The molecular backbone may additionally provide a means for absorption of analyte within the film thickness. Example SAMs include: (1) mercapto-undecanoic acid/Cu (II) for organophosphorus compounds; (2) octadecyithiol for hydrocarbons, especially aromatics; and (3) chlorinated decylthiol for chlorinated hydrocarbons. If a hydroxylated surface such as silica is used, a derivatized silane can be used to form a SAM.

L-B films are formed by dip or spray application of a dilute solution of a material that forms bilayers. The layers may be built up by repeated application to form relatively thick coatings that may absorb significant quantities of analyte. Hence, higher sensitivities may be possible using LB films. An example coating is fluoropolyol. This material forms multiple bilayer coatings and can absorb hydrocarbons such as dimethylmethyl phosphonate and other organophosphorus compounds. The selectivity against water vapor is 20,000 to 1.

Adsorption can be reversible or irreversible based on coating chemistry. A representative reversible example is: dimethylmethyl phosphonate absorption in a fluoropolyol film. A representative irreversible example is an amalgam of mercury on gold. If rapid response and recovery are desired, films which are only a few monolayers thick are required. Thicker films may be used to increase sensitivity or dynamic range.

For a microcantilever 12 having a density p, an area A, a Young's Modulus E, and an area moment of Inertia I, the equation of motion for vibration perpendicular to the major axis (long axis) is given by:

$$EI\frac{\partial^4 z}{\partial y^4} + \rho A \frac{\partial^2 z}{\partial t^2} = 0 \qquad (1)$$

The frequency of vibration for the microcantilever 12, $\omega_n$ for the $n^{th}$ harmonic, is given by:

$$\omega_n = k_n^2 \sqrt{\frac{EI}{\rho A}} \quad n = 1, 2, 3 \ldots \qquad (2)$$

The values of $K_n l$ are $$K_n l = 1.875, 4.694, 7.855, \ldots \frac{(2n-1)}{2} \pi \qquad (3)$$

where K is the wave vector and l is the length of the cantilever.

The moment of inertia I is given by $$I = \frac{wt^3}{12} \qquad (4)$$

where w is the width and t is the thickness of the beam. The beam can be approximated as a spring of a spring constant k $$k = \frac{Ewt^3}{4l^3} = \frac{3EI}{l^3} \qquad (5)$$

The resonance frequency of the cantilevers $$v = \frac{W}{2\pi} = \frac{1}{2\pi} \sqrt{\frac{k}{M^*}} \qquad (6)$$

where the effective mass $M^* = 0.24M$, where M is the mass of the cantilever.

The above relationship illustrates that resonance frequency is inversely proportional to the square root of the mass. Consequently, if a mass of material is added to the surface, the resonance frequency will change. For a uniformly deposited mass change, $\Delta m$, due to adsorption $$\Delta m = \frac{k}{4\pi^2 0.24} \left( \frac{1}{v_1^2} - \frac{1}{v_2^2} \right) \qquad (7)$$

where $v_1$ and $v_2$ are the resonance frequency before and after adsorption.

Figure 5:
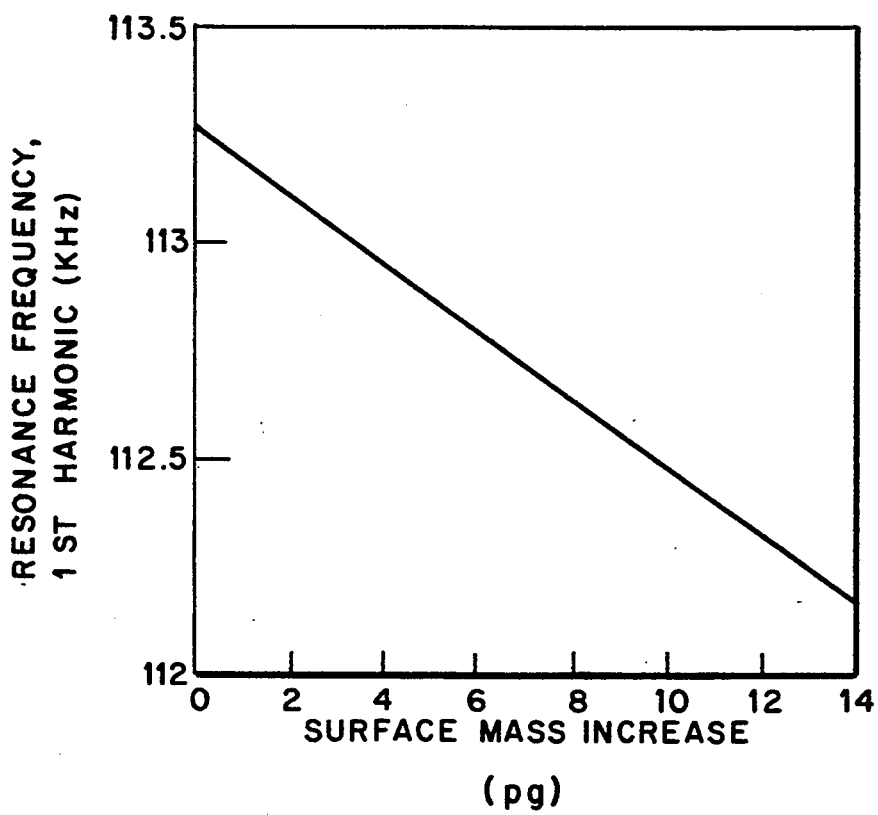
FIG. 5 is a graph which illustrates the inverse correlation between mass increases to a resonantly vibrating element and the frequency of that resonance.

A hypothetical example of the invention having a 200 μm long, 50 μm wide and 3-μm thick microcantilever 12 weighing 700 pg as composed of silicon, will have a first harmonic resonance frequency of about 113 kHz. The effect of added surface mass to this vibrating system is illustrated by the graph of FIG. 5. For this example, sensitivities much better than 1 pg are achievable for measurement times much less than 1 sec. which means that the device is at least 3 orders of magnitude more sensitive than a comparable SAW device.

Figure 2:
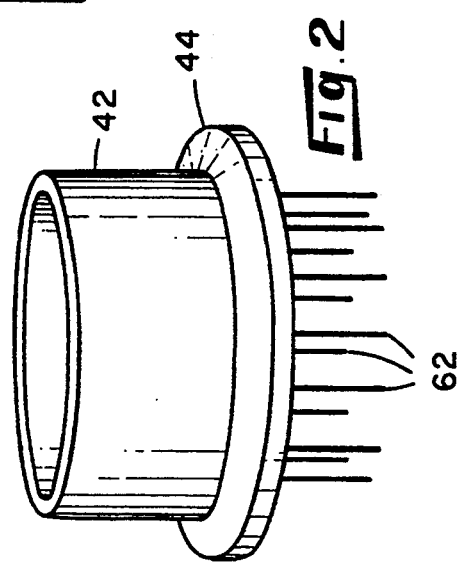
FIG. 2 is a representative invention instrument assembly.
Figure 3:
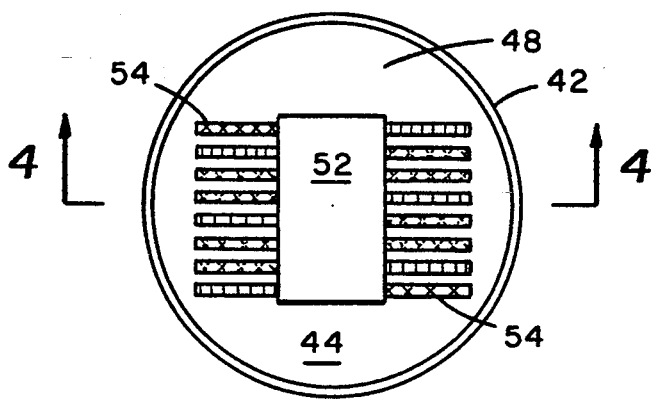
FIG. 3 is a plan view of the invention instrument assembly.
Figure 4:
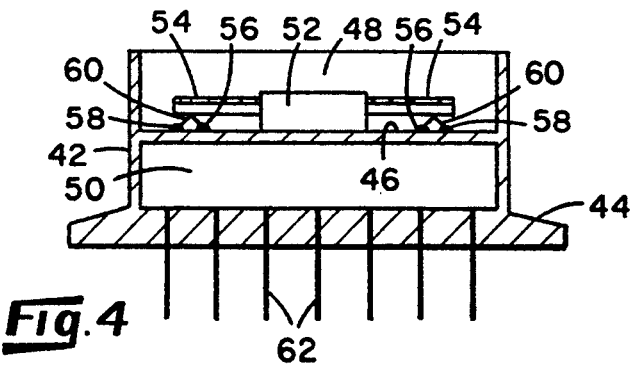
FIG. 4 is a sectional elevation of the invention instrument assembly. As viewed along cutting plane 4—4 of FIG. 3.

The invention embodiment illustrated by FIGS. 2, 3 and 4 is representative of a 16 sensor array of coated microcantilevers, each with different absorption/adsorption characteristics. Within an open ended cylinder 42 of 0.5 in. dia. by 0.5 in. height supported by a flanged base 44, a transverse partition 46 separates an outer, sensor volume 48 from a sealed, interior circuit volume 50. A single piezoelectric transducer 52 drives 16 microcantilevers 54. However, each microcantilever surface is distinctively coated as described herein.

Beneath the oscillating end of each microcantilever 54 is a laser diode 56 and photodiode 58 for respectively emitting and receiving laser beams 60 reflected from respective microcantilevers 54. Integrated microprocessor circuitry within the circuit volume 50 receives the raw photodiode 58 signals for development of respective, frequency differential signals at leads, 62.

These several, distinctive signals leads 62 are connected with data processor terminals for pre-programmed analysis. Response patterns from several sensors are characteristic of the chemical or chemical combination present in the monitored vapor. Pattern recognition software may be developed for response to patterns that correspond to hazardous conditions.

Another significant advantage of an array system is that it can easily identify a number of hazardous vapor conditions that is far in excess of the number of sensors in the array. Furthermore, as new hazards arise, it is feasible to make the instrument responsive to them by changing only the pattern recognition software.

From the foregoing disclosure, it will be appreciated that a cantilever plate may be utilized in lieu of the microcantilevered bars 12 or 54 thereby raising the surface-to-volume ratio for greater sensitivity.

Additionally, sensor frequency may be measured by means other than the photo detection method previously described. By one such other method, a silicon or GaAs cantilever is fabricated with piezoresistive properties. The electrical resistance of the cantilever changes under beam flexure. The resonant frequency may be monitored as a cantilever resistance signal.

Another sensor frequency monitoring method relies upon capacitance synchronization using a parallel matched structure located a short distance away from the moving structure.

Either of these alternative frequency measuring methods would make the instrument more compact, durable, less expensive to manufacture, and eliminate the need for separate optoelectric devices.

The above described sensor can be modified to operate under liquid either by vibrating the cantilever directly or by setting the cantilever into oscillation by mechanically moving the liquid surrounding the cantilever and observing the changes in frequency corresponding to maximum amplitude.

Having fully disclosed our invention, those of ordinary skill in the art will recognize obvious alternatives and equivalents as our invention however,

We claim:

1. An apparatus for detecting the presence of a predetermined vapor phase chemical in a monitored atmosphere comprising:
   a piezoelectric transducer having a least one cantilevered spring element secured thereto, said spring element having an area thereof coated with a chemical having an affinity for said predetermined vapor phase chemical;
   oscillator means for stimulating said transducer at or about a resonant vibrational frequency of said cantilevered spring element; and,
   vibration detection means comprising photo-detection means for emitting a signal in synchronization with said spring element vibration for measuring a vibrational frequency change in said spring element due to a change in the vibrated mass of said spring element.

2. An apparatus as described by claim 1 wherein said vibration detection means comprises a laser diode for emitting a laser beam and a photodiode for detecting, said laser beam, said laser diode being disposed to emit said laser beam against said vibrating spring element.

3. An apparatus as described by claim 2 wherein said photodiode is disposed for detecting a reflection of said laser beam from said spring element and emitting signals corresponding to the vibrational frequency of said spring element.

4. An apparatus as described by claim 1 wherein said vibration detection means comprises a first counting circuit for measuring the transducer stimulation frequency of said oscillator means, a second counting circuit for measuring said spring element vibrational frequency and a differentiating circuit for determining a frequency differential between said stimulation frequency and said spring element vibrational frequency.

5. An apparatus for detecting the presence of a predetermined vapor phase chemical in a monitored atmosphere comprising:
   a piezoelectric transducer having at least one cantilevered spring element secured thereto, said spring element having an area portion along substantially the entire length thereof coated with a chemical having an affinity for said predetermined vapor phase chemical;
   oscillator means for stimulating said transducer at or about the resonant vibrational frequency of said cantilevered spring element; and,
   vibration detection means for measuring a vibrational frequency change in said spring element due to a change in the vibrated mass of said spring element.

6. A method for detecting the presence of a predetermined vapor phase chemical in a monitored atmosphere comprising the steps of:
   fabricating a cantilever spring element having a structural base secured to a piezoelectric transducer;
   coating a surface portion of said spring element along substantially the entire length thereof with a chemical having an affinity for said predetermined vapor phase chemical;
   electrically driving said transducer at or near a resonance frequency of said spring element.
   exposing said coated and driven cantilever spring element to a monitored atmosphere,
   measuring a vibrational frequency change of said cantilever spring element over a predetermined time period in said monitored atmosphere; and
   relating said vibrational frequency change to a concentration value of said predetermined vapor phase chemical in said monitored atmosphere.

7. A method as described by claim 6 wherein a first signal that is proportional to the vibrational frequency of said spring element is generated by the reflection of a laser beam from the surface of said spring element.

8. A method as described by claim 7 wherein said first signal is generated by a photodiode in response to a cyclic stimulation from said reflected laser beam.

9. A method as described by claim 8 wherein said laser beam is generated by a laser diode.

10. A method as described by claim 9 wherein a second signal is generated that is proportional to the driving frequency of said transducer.

11. A method as described by claim 10 wherein said first and second signals are compared to generate a differential signal proportional to the frequency difference between first and second signal.

12. A method as described by claim 11 wherein said differential signal is related to a known mass accumulation of said predetermined vapor phase chemical on said chemically coated portion of said spring element.

13. A method as described by claim 7 wherein said transducer vibrates a plurality of spring elements.

14. A method as described by claim 13 wherein each of said plurality of spring elements is provided with a distinctive chemical coating having affinity for a respectively distinctive vapor phase chemical.

15. A method as described by claim 14 wherein the vibrational frequency of each of said plurality of spring elements is independently measured.

16. A method as described by claim 15 wherein first signals proportional to each of said independent frequency measurements are directed to a microprocessor for preprogrammed pattern recognition analysis.

17. An apparatus for detecting the presence of a predetermined vapor phase chemical in a monitored atmosphere comprising:
   a piezoelectric transducer having a plurality of cantilevered spring elements secured thereto, each of said spring elements having substantially the same resonant vibrational frequency and a respective area thereof coated with a chemical having an affinity for a predetermined vapor phase chemical;
   oscillator means for stimulating said transducer at or about the resonant vibrational frequency of said cantilevered spring elements
   vibration detection means for measuring a vibrational frequency change respective to each of said plurality of spring elements due to a change in the vibrated mass respective to each spring element.

18. An apparatus as described by claim 17 wherein said vibration detection means comprises means respective to each of said spring elements for emitting a signal in synchronization with said respective spring element vibration.

19. An apparatus as described by claim 17 wherein said vibration detection means comprises a laser diode for emitting a laser beam and a photodiode for detecting said laser beam, said laser beam diode being disposed to emit said laser beam against said vibrating spring element.

20. An apparatus as described by claim 19 wherein said photodiode is disposed for detecting a reflection of said laser beam from said spring element and emitting signal corresponding to the vibrational frequency of said spring element.

* * * * *